United States Patent [19]
Osswald et al.

[11] Patent Number: 5,997,536
[45] Date of Patent: Dec. 7, 1999

[54] HEART CATHETER WITH AN ELECTRODE ON A SPREADABLE DEVICE

[75] Inventors: Stefan Osswald, Basel, Switzerland; Daniel Baumgartner, Grenzach-Wyhlen; Andreas Eberhart, Lörrach, both of Germany

[73] Assignee: Sulzer Osypka GmbH, Grenzach-Wyhlen, Germany

[21] Appl. No.: 08/967,499

[22] Filed: Nov. 11, 1997

[30] Foreign Application Priority Data

Nov. 13, 1996 [EP] European Pat. Off. .............. 96810784

[51] Int. Cl.$^6$ .............................. A61N 1/05; A61B 17/39
[52] U.S. Cl. ............................ 606/47; 607/122; 607/101; 600/374
[58] Field of Search ..................... 607/122, 101; 600/373–375, 381; 606/41, 47

[56] References Cited

U.S. PATENT DOCUMENTS

| | | |
|---|---|---|
| 5,007,908 | 4/1991 | Rydell . |
| 5,702,438 | 12/1997 | Avitall ...................... 607/122 |
| 5,738,683 | 4/1998 | Osypka ...................... 607/47 |
| 5,782,899 | 7/1998 | Imran ...................... 607/122 |
| 5,830,210 | 11/1998 | Rudko et al. .............. 606/15 |
| 5,836,947 | 11/1998 | Fleischman et al. ...... 606/47 |

FOREIGN PATENT DOCUMENTS 0 573 311 A1  12/1993  European Pat. Off. .
0 727 183 A1  8/1996   European Pat. Off. .

*Primary Examiner*—Jeffrey R. Jastrzab
*Attorney, Agent, or Firm*—Townsend and Townsend and Crew LLP

[57] ABSTRACT

The heart catheter has at least one electrode pole, which is arranged on a spreadable device at the distal end of a catheter shaft. The device comprises at least two struts manufactured from an elastic material, which can be spread out following the contours of a cavity of the heart, in particular of a vestibule. Means are provided with which the electrode pole is displaceable along a strut.

13 Claims, 2 Drawing Sheets

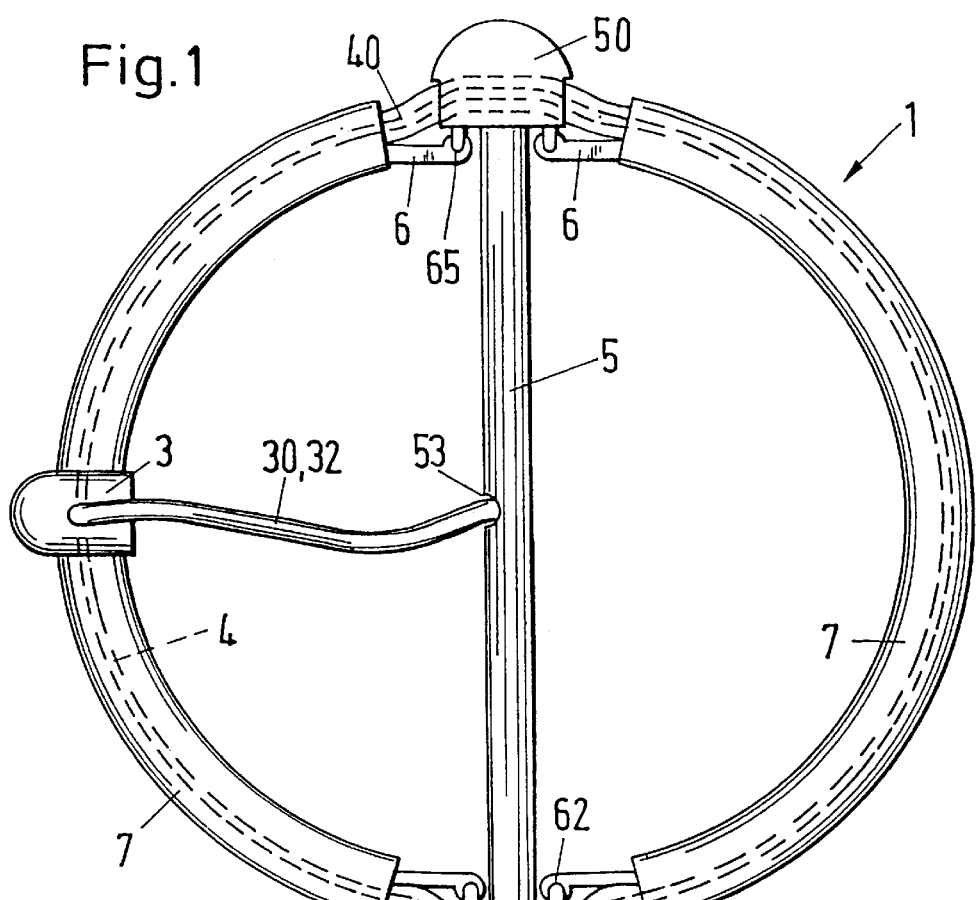
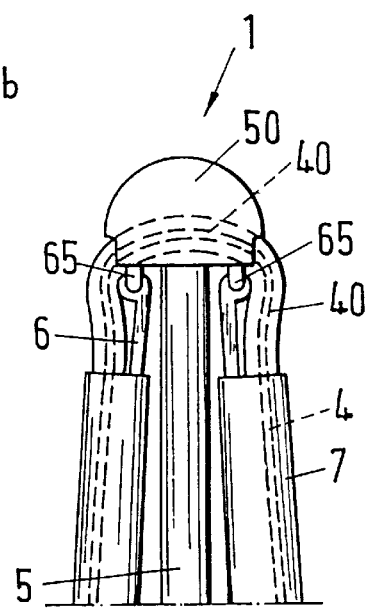
Fig.1
Fig.2

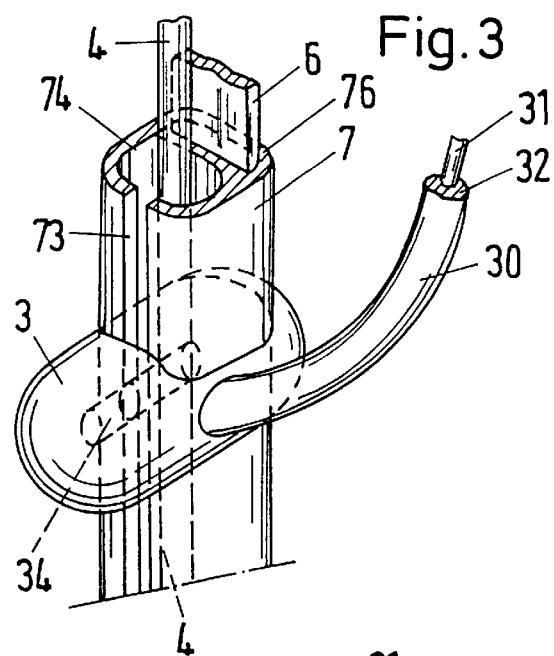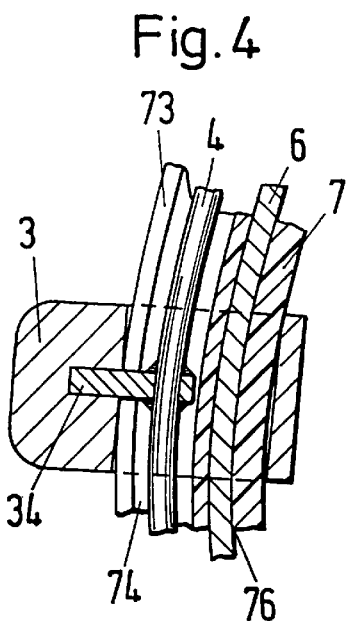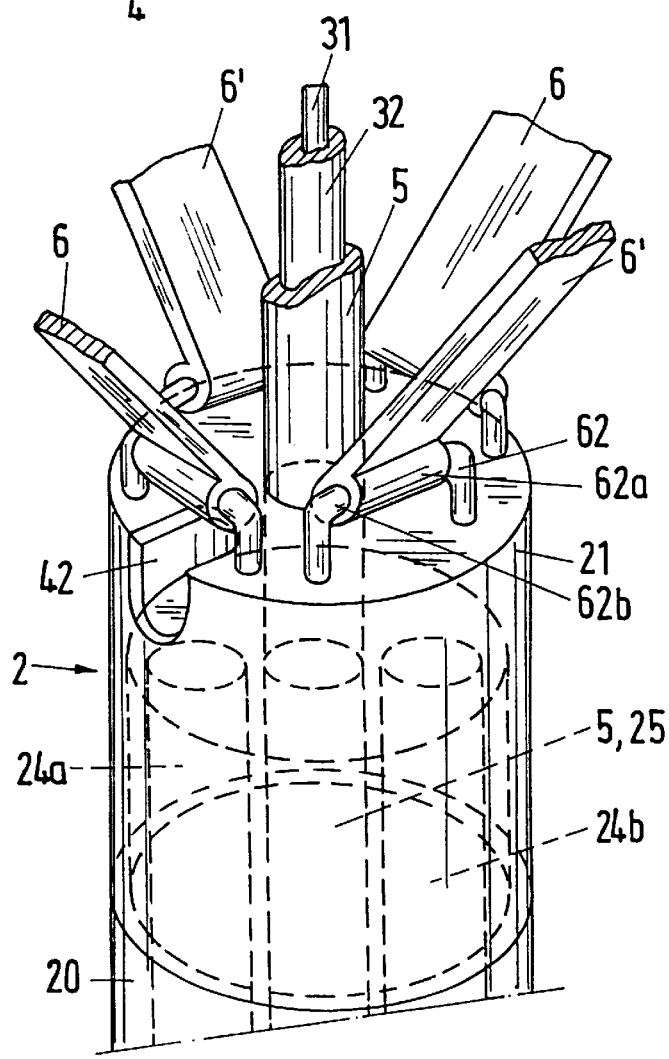

HEART CATHETER WITH AN ELECTRODE ON A SPREADABLE DEVICE

BACKGROUND OF THE INVENTION

The invention relates to a heart catheter with an electrode on a spreadable device.

A heart catheter of this kind is known from the patent specification U.S. Pat. No. 5,263,493. A spreadable device comprising two struts is arranged in the region of the distal end of this catheter; a plurality of individually controllable electrode poles is located on the struts. In a non spread state of the electrode device, the catheter can be inserted via a blood vessel into a cavity of the heart. The electrode device is spread out in the heart, so that the poles of the electrode come into contact with the inner surface of the cavity. Heart potentials can be measured with the electrode poles (endocardial mapping). They can also be used for the carrying out of ablations in a vestibule of the heart.

SUMMARY OF THE INVENTION

The object of the invention is to provide a heart catheter which is particularly suitable for the carrying out of ablations.

The heart catheter has at least one electrode pole, which is arranged on a spreadable device at the distal end of a catheter shaft. The apparatus comprises at least two struts manufactured from an elastic material, which are spread to follow the contours of a cavity of the heart, in particular of a vestibule. Means are provided with which the pole of the electrode is displaceable along a strut. With the movable electrode pole, connected ablation lines can be drawn successfully on the inner surface of the heart (line lesions).

BRIEF DESCRIPTION OF THE DRAWINGS

FIG. 1 is a partial cross-sectional view illustrating the electrode device arranged at the distal end of a heart catheter, in a spread-out state, FIG. 2 shows the electrode device in a spread-out state, wherein merely one region of the head part is illustrated, FIG. 3 is a perspective view illustrating the electrode pole movable on a strut, FIG. 4 is a section through an electrode pole, and FIG. 5 is a perspective view illustrating joint connections of the struts at the distal end of the catheter shaft.

DESCRIPTION OF THE PREFERRED EMBODIMENTS

The distal end of a heart catheter in accordance with the invention, which is illustrated in FIG. 1, comprises the following components: a spread-out electrode device 1 at the distal end of a catheter shaft 2; a displaceable electrode pole 3, which is movable with a loop-like draw thread 4; a guide tube 5; and struts 6 with guides 7 in the form of profiled hose sections.

The catheter shaft 2 consists of a tube 20 with a plurality of lumens and a shaft sleeve 21. The guides 7 for the draw thread 4, which is connected with the pole of the electrode 3, are arranged along two struts 6 lying opposite one another. The two continuations 4' and 4" of the loop-like draw thread 4 are guided by two lumens 24a and 24b of the catheter shaft 2 to a proximal end of the catheter (not shown).

The catheter shaft 2 contains, at least at its distal end region, a lumen 25 for the guide tube 5, which is displaceable in the lumen 25 and partially protrudes therefrom. The struts 6 are arranged between a head sleeve 50 at the distal end of the guide tube 5 and the distal end of the catheter shaft 2. They are connected via joints 65 with the head sleeve 50 and via joints 62 with the shaft sleeve 21. The device 1 can be altered by movement of the guide tube 5 into the lumen 25 or out of it from an extended state (FIG. 2) into a basket-like state (FIG. 1) or vice versa.

In the head region of the device 1, the draw thread 4 is guided by a tube 40 connecting the two guides 7, which is inserted into the head sleeve 50. Corresponding transition pieces at the other ends of the guides 7 are formed by hoses 41a and 41b, which open out into the lumens 24a or 24b respectively.

An electrical lead enclosed in a protective tube 25 is arranged coaxially in the guide tube 5, which maintains a flexible connection 30 between an aperture 53 in the exposed part of the guide tube 5 and the pole of the electrode 3.

In the regions of the struts 6, the draw thread 4 is respectively inserted in a lumen 74 of the guide 7, which is formed as a profiled hose section 7; see FIG. 3. The profiled hose section 7 has a second lumen 76, through which the strut 6 passes and thus produces an attachment of the guide 7 onto the associated strut 6. The electrical connection 30 is mounted on one side of the pole of the electrode 3. As can be seen from the sectional drawing in FIG. 4, the pole of the electrode 3 is connected with the draw thread 4 by means of a follower 34. A groove 73 is provided for the passage of the follower 34 in the profiled hose section 7.

As FIG. 5 shows, four struts 6, 6' are provided, which form two pairs of diametrically arranged struts 6 and 6' respectively. The pair with the struts 6 carries the means, namely the guides 7 and the draw thread 4, with which the pole of the electrode 3 is displaceable along one of the two struts 6.

The struts 6, 6' are fastened to the cover plate of the =shaft sleeve 21 by means of sleeves 62a and pins 62b of the joints 62. Corresponding fastening means with joints 65 are provided at a joint plate at the base of the head sleeve 50. The manner of fastening with joints 62, 65 enables an orthogonal spreading out of the struts 6, 6' with regard to the shaft of the catheter 2. The orthogonal spreading out results in a ball shape of the device 1 (see FIG. 1). Through the ball shape, the vestibule which is to be treated is ideally filled out and also spanned.

Not shown in FIG. 5 are the pieces of hose 41a and 41b for the draw thread 4 (see FIG. 1) and the guides 7. The inserted piece of hose 41a would establish a connection from the lumen 24a through the aperture 42 to the lumen 74 (see FIG. 3) of the guide 7.

The struts 6, 6' are essentially formed in the shape of flexible, straight strips, wherein the long side of the rectangular strut cross-section lies in a perpendicular and tangential direction to the shaft axis of the catheter. The struts 6, 6' are advantageously manufactured from a metallic alloy (from "Elgiloy" for example). The strut cross-section can also be round, for example circular or elliptical.

The number of the struts 6 can also be larger or smaller than four, but it must be at least two. There can also be more than one pole of the electrode 3 provided—arranged on the same struts or on different ones.

The pole of the electrode 3 in accordance with FIG. 3 is formed in such a way that it is guided on the surface of the profiled hose section 3. A rail (not illustrated) can also be used for guiding the pole of the electrode 3.

The electrical connection 30 can also be established along the struts 6 by, for example, so forming the draw thread that it contains the electrical lead 31. In this case the lumen of the guide tube 5 can be used for the reception of a guide wire, with the help of which the heart catheter can be pushed through the blood vessels to the heart and into the latter.

If no guide wire is used for the insertion of the catheter into the heart, then it is advantageous if a flexible 2 to 3 cm long tip (not illustrated) is provided at the distal end of the head sleeve 50. This tip facilitates the insertion of the catheter.

The pole of the electrode 3 is connectable via the connection 30 to a regulated energy source (high frequency RF) suitable for the carrying out of an ablation, outside the body of the patient. To this end the pole 3 is advantageously equipped with a thermosensor (thermocouple, thermosister). Apart from the electrical lead 31, the connection 30 additionally contains two connection leads to the thermosensor.

At least one second means for carrying out diagnostic and/or therapeutic heart operations can also be provided, which is insertable into the heart by means of a separate lumen of the catheter shaft (not illustrated). At the same time, the use of a strut as a guide aid can be advantageous. An example for the named second means is an electrode catheter, with which heart potentials can be sensed.

What is claimed is:

1. A heart catheter comprising:
    a catheter shaft having a distal end;
    a guide tube having a distal end and being slidably coupled with the catheter shaft to protrude from the distal end of the catheter shaft;
    a spreadable device including a plurality of struts coupled between the distal end of the catheter shaft and the distal end of the guide tube, the struts being spreadable to follow contours of a cavity of a heart;
    an electrode slidably coupled with one of the struts; and
    an electrical line protruding from an interior of the guide tube through an aperture in the guide tube and being coupled with the electrode.
2. The heart catheter according to claim 1 further comprising:
    a pair of guides coupled with two of the plurality of struts; and
    a draw thread slidably coupled with the pair of guides, the draw thread being connected with the electrode slidably coupled with the strut which is coupled with one of the two guides to displace the electrode along the strut.
3. The heart catheter according to claim 2 wherein the guides include lumens for guiding the at least one draw thread.
4. The heart catheter according to claim 1 wherein the struts are elastic.
5. The heart catheter according to claim 1 wherein the electrical line includes a protective sheath.
6. The heart catheter according to claim 1 wherein the draw thread includes two ends extending through two lumens in the catheter shaft out a proximal end of the catheter shaft.
7. The heart catheter according to claim 1 wherein the catheter shaft includes a lumen at least in a region near the distal end for accommodating the guide tube, the guide tube being displaceable in the lumen and partially protruding from the lumen through the distal end of the catheter shaft, and wherein the spreadable device is changeable between an extended state and a basket-like state by movement of the guide tube relative to the catheter shaft.
8. The heart catheter according to claim 1 further comprising a head sleeve disposed at the distal end of the guide tube, wherein the catheter shaft includes a shaft sleeve, wherein the struts are each connected at one end with the head sleeve via joints and at the other end with the shaft sleeve.
9. The heart catheter according to claim 1 wherein the spreadable device includes two pairs of respectively diametrically arranged struts.
10. The heart catheter according to claim 9 further comprising a pair of guides coupled with one pair of struts and a draw thread slidably coupled with the pair of guides, the draw thread being connected with the electrode slidably coupled with one of the pair of struts to displace the electrode along the strut.
11. The heart catheter according to claim 1 wherein the struts comprise generally straight flexible strips made of a metallic alloy.
12. The heart catheter according to claim 11 wherein the struts are rectangular in cross-section.
13. The heart catheter according to claim 1 wherein the electrode is connectable to a regulated energy source suitable for carrying out an ablation and located outside a patient's body.

* * * * *